US010653715B2

(12) United States Patent
Ryazanov et al.

(10) Patent No.: US 10,653,715 B2
(45) Date of Patent: *May 19, 2020

(54) METHODS AND COMPOSITIONS FOR EXTENDING LIFESPAN

(71) Applicant: Longevica Therapeutics Inc., Princeton, NJ (US)

(72) Inventors: Alexey Ryazanov, Princeton, NJ (US); Alexander Chikunov, Princeton, NJ (US); Yuriy Shymkiv, Middlesex, NJ (US)

(73) Assignee: Longevica Theraputics Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/787,398

(22) Filed: Oct. 18, 2017

(65) Prior Publication Data

US 2018/0104275 A1    Apr. 19, 2018

Related U.S. Application Data

(60) Provisional application No. 62/410,378, filed on Oct. 19, 2016.

(51) Int. Cl.

| A61K 31/733 | (2006.01) |
|---|---|
| A61K 33/06 | (2006.01) |
| A23L 33/105 | (2016.01) |
| A61K 31/194 | (2006.01) |
| A61K 31/198 | (2006.01) |
| A61K 31/216 | (2006.01) |
| A61K 33/14 | (2006.01) |
| A61K 45/06 | (2006.01) |

(52) U.S. Cl.
CPC .......... *A61K 31/733* (2013.01); *A23L 33/105* (2016.08); *A61K 31/194* (2013.01); *A61K 31/198* (2013.01); *A61K 31/216* (2013.01); *A61K 33/06* (2013.01); *A61K 33/14* (2013.01); *A61K 45/06* (2013.01); *A23V 2002/00* (2013.01); *A23V 2250/032* (2013.01); *A23V 2250/161* (2013.01); *A23V 2250/21* (2013.01); *A23V 2250/5062* (2013.01); *A61K 2300/00* (2013.01)

(58) Field of Classification Search
None
See application file for complete search history.

(56) References Cited

U.S. PATENT DOCUMENTS

| 6,255,341 | B1 * | 7/2001 | DeMichele | A23L 33/12 |
|---|---|---|---|---|
| | | | | 424/600 |
| 6,310,051 | B1 * | 10/2001 | Karlsson | A61K 31/198 |
| | | | | 514/188 |
| 7,258,879 | B1 | 8/2007 | Hodge | |
| 2004/0001817 | A1 * | 1/2004 | Giampapa | A61K 31/198 |
| | | | | 424/94.1 |
| 2006/0040001 | A1 * | 2/2006 | Johnson | A23L 2/52 |
| | | | | 424/727 |
| 2008/0058292 | A1 * | 3/2008 | Tawakol | A61K 9/4866 |
| | | | | 514/161 |
| 2011/0206650 | A1 * | 8/2011 | De Haen | A61K 9/0034 |
| | | | | 424/93.45 |
| 2012/0000333 | A1 | 1/2012 | Hatcher et al. | |
| 2015/0051235 | A1 | 2/2015 | Bannister | |
| 2016/0129056 | A1 * | 5/2016 | Heck | A61K 35/747 |
| | | | | 424/93.45 |

FOREIGN PATENT DOCUMENTS

| RU | 2404788 | 11/2010 |
|---|---|---|
| RU | 2555471 | 7/2015 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
de Attayde, M. J. P. M., Florêncio, G. L. D., Gabiatti, J. R. E., do Amaral, R. L., Júnior, J. E., & da Silveira Goncalves, A. K. (2011). Perinatal morbidity and mortality associated with chlamydial infection: a meta-analysis study. The Brazilian Journal of Infectious Diseases, 15(6), 533-539. (Year: 2011).*
Paciocco, G., Martinez, F. J., Bossone, E., Pielsticker, E., Gillespie, B., & Rubenfire, M. (2001). Oxygen desaturation on the six-minute walk test and mortality in untreated primary pulmonary hypertension. European Respiratory Journal, 17(4), 647-652. (Year: 2001).*
International Search Report dated Dec. 1, 2016 in connection with PCT International Application Publication No. WO 2016/168670 A3.
International Search Report dated Feb. 28, 2018 in connection with PCT International Application Publication No. WO 2018/075641 A1.
Steinbaugh et al. (2012) "Activation of genes involved in xenobiotic metabolism is a shared signature of mouse models with extended lifespan." American Journal of Physiology Endocrinology and Metabolism 303(4):488-95.
Chelates Product Guide, Dissolvine master the elements (Sep. 2010).

(Continued)

*Primary Examiner* — Dale R Miller
(74) *Attorney, Agent, or Firm* — Gary J. Gershik; Cooper & Dunham LLP

(57) ABSTRACT

The present invention relates to methods for attenuating aging, of health maintenance, and/or treating, or delaying the onset of, an age-related condition or disorder, in a subject comprising administering to the subject an effective amount of (a) one or more compounds that sustain pharmacological activation of xenobiotic metabolism or induce fermentation by gut bacteria to produce substances that activate xenobiotic metabolism enzymes and/or stimulate xenobiotic excretion and (b) one or more chelators. A further aspect of the invention is a composition comprising (a) and (b).

11 Claims, 8 Drawing Sheets

(56) References Cited

OTHER PUBLICATIONS

May 3, 2019 Non-Final Office Action issued in connection with U.S. Appl. No. 15/784,869.
Galanello, R., & Origa, R. (2010). Beta-thalassemia. *Orphanet journal of rare diseases*, 5(1), 11.
Michaelis, M., et al. (2004). Pharmacological activity of DTPA linked to protein-based drug carrier systems. *Biochemical and biophysical research communications*, 323(4), 1236-1240.
Smith, R. S. (1964). Chelating agents in the diagnosis and treatment of iron overload in thalassemia. *Annals of the New York Academy of Sciences*, 119(2), 776-788.

* cited by examiner

METHODS AND COMPOSITIONS FOR EXTENDING LIFESPAN

This application claims the benefit of U.S. Provisional Application No. 62/410,378, filed Oct. 19, 2016, the entire contents of which are hereby incorporated by reference.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

FIELD OF THE INVENTION

The present invention relates to methods for attenuating aging, of health maintenance, and/or treating, or delaying the onset of, an age-related condition or disorder, in a subject comprising administering to the subject an effective amount of (a) one or more compounds that sustain pharmacological activation of xenobiotic metabolism or induce fermentation by gut bacteria to produce substances that activate xenobiotic metabolism enzymes and/or stimulate xenobiotic excretion and (b) one or more chelators. A further aspect of the invention is a composition comprising (a) and (b).

BACKGROUND OF THE INVENTION

It is highly desirable to attenuate aging and extend human lifespan, but the complex etiology of aging leaves potential drug targets unclear. While treatments exist for some symptoms of age related disorders, no treatments are available that address all aspect of aging simultaneously. There is, therefore a need for new treatment to extend lifespan and treat, or delay the onset of, age-related conditions and disorders.

Xenobiotic metabolism is a complex, highly regulated and energetically costly process whose major function is biotransformation and elimination from the body of lipophilic toxic molecules that are generated as products of metabolism (endobiotics) or absorbed from the environment (xenobiotics). This process involves a large battery of enzymes, mainly expressed in the liver and the gastrointestinal tract and transcriptionally regulated by several nuclear receptors (NRs). Phase I xenobiotic metabolism enzymes, such as cytochrome P450s, catalyze biotransformation reactions (e.g. hydroxylation) to functionalize the chemically inert xenobiotic molecules for further modifications that occur during Phase II. Phase II enzymes (including UDP-glucuronosyltransferases and glutathione transferases) catalyze covalent attachment of polar side groups to functionalized xenobiotic molecules, increasing their solubility and promoting their excretion.

Slowing down aging is predicted to yield greater benefits for human health than curing cancer and heart disease combined (Goldman 2013). Despite significant progress in recent years, the underlying biochemical pathways that determine longevity are not fully understood.

SUMMARY OF THE INVENTION

This invention provides a dietary supplement or food or beverage product comprising:
(a) one or more compounds that sustain the pharmacological activation of xenobiotic metabolism or induce fermentation by gut bacteria to produce substances that activate xenobiotic metabolism enzymes and/or stimulate xenobiotic excretion; and
(b) one or more chelators.

This invention provides a dietary supplement or food or beverage product comprising:
(a) Inulin; and
(b) Citric acid.

This invention also provides a dietary supplement or food or beverage product comprising:
(a) Inulin; and
(b) Lemon or lime extract, DTPA, EDTA, St. John's wort extract, Hyperforin, Ginkgo bilogoba extract, Ginkgolide A or B, vitamin C, Ascorbic acid 6-palmitate, Pantothenic acid (vitamin B-5), Niacinamide, Allicin (garlic), Lactobionate, Melatonin, Metformin, L-Dopa, extract Mucuna beans (Mucuna Dopa), L-Histidine, Quercetin, Curcumin, L-Glutamic acid, succinic acid, N-Acetil Cysteine, Green tea extract, Epigallocatechin-3-gallaye, Glutathione, Aspirin, Salicylate, Glycine, Resveratrol, Genistein, Garnosine, Rapamycin, Lipoic acid, or Taurine.

This invention also provides a dietary supplement or food or beverage product comprising:
(a) Inulin;
(b) St. John's wort extract, Hyperforin, Ginkgo bilogoba extract, or Ginkgolide A or B, Rapamycin; and
(c) Citric acid.

This invention also provides a method of attenuating aging, of health maintenance, and/or treating or delaying the onset of, an age-related condition or disorder, the method comprising administering to the subject an effective amount of:
(a) one or more compounds that sustain the pharmacological activation of xenobiotic metabolism or induce fermentation by gut bacteria to produce substances that activate xenobiotic metabolism enzymes and/or stimulate xenobiotic excretion; and
(b) one or more chelators.

DETAILED DESCRIPTION OF THE INVENTION

Definitions

Figure 1A:
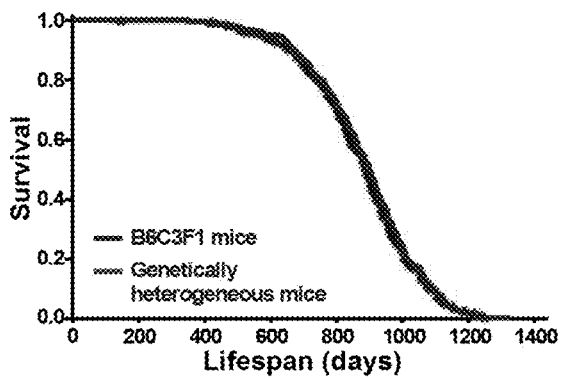
FIG. 1A—Survival curves of B6C3F1/J mice are identical to genetically heterogeneous mice used in the NIH interventions testing program (Miller 2011)
Figure 1B:
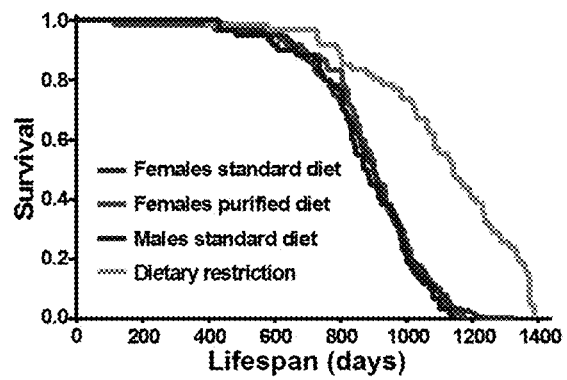
FIG. 1B—Effects of gender and diet on lifespan of B6C3F1/J mice. Lifespan was not affected by gender or by switching the mice to a purified, chemically defined diet. Consistent with previous reports, dietary restriction significantly extended lifespan.

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means ±10% of the numerical value or range recited or claimed, unless the context requires a more limited range.

The phrase "extending the lifespan" includes statistically significantly increasing the life expectancy of a subject (e.g., compared to a control group).

"Therapeutically effective amount" refers to that amount of a compound of the invention that, when administered to a mammal, is sufficient to effect treatment, as defined below, of a disease or condition in the mammal. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest, e.g., tissue injury, in a mammal, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Embodiments

This invention provides a dietary supplement or food or beverage product comprising:
  (a) one or more compounds that sustain the pharmacological activation of xenobiotic metabolism or induce fermentation by gut bacteria to produce substances that activate xenobiotic metabolism enzymes and/or stimulate xenobiotic excretion; and
  (b) one or more chelators.

In one aspect of the invention (a) is inulin.

In one aspect of the invention (a) is an agonist of nuclear receptors that activate xenobiotic metabolism.

In one aspect of the invention the agonist of nuclear receptors that activate xenobiotic metabolism is selected from the group consisting of constitutive androstane receptor (CAR) agonists, pregnane X receptor (PXR) agonists, or a peroxisome proliferator-activated receptor α (PPARα) agonist.

In one aspect of the invention the agonist of nuclear receptors that activate xenobiotic metabolism is clofibrate.

In one aspect of the invention (b) is diethylenetriaminepentaacetic acid (DTPA).

This invention also provides a dietary supplement or food or beverage product comprising:
  (a) Inulin; and
  (b) Citric acid.

In one aspect of the invention the dietary supplement or food or beverage further comprises magnesium or a magnesium salt.

In one aspect of the invention the dietary supplement or food or beverage product comprises, per serving:
  (a) 5-10 grams of inulin; and
  (b) 1-2 grams of citric acid.

In one aspect of the invention the dietary supplement or food or beverage product comprises 200-300 milligrams of magnesium or a magnesium salt per serving.

In one aspect of the invention the dietary supplement or food or beverage product comprises 250 milligrams of magnesium or a magnesium salt per serving.

This invention also provides a dietary supplement or food or beverage product comprising:
(a) Inulin; and
(b) Lemon or lime extract, DTPA, EDTA, St. John's wort extract, Hyperforin, Ginkgo bilogoba extract, Ginkgolide A or B, vitamin C, Ascorbic acid 6-palmitate, Pantothenic acid (vitamin B-5), Niacinamide, Allicin (garlic), Lactobionate, Melatonin, Metformin, L-Dopa, extract Mucuna beans (Mucuna Dopa), L-Histidine, Quercetin, Curcumin, L-Glutamic acid, succinic acid, N-Acetil Cysteine, Green tea extract, Epigallocatechin-3-gallaye, Glutathione, Aspirin, Salicylate, Glycine, Resveratrol, Genistein, Garnosine, Rapamycin, Lipoic acid, or Taurine.

In one aspect this dietary supplement or food or beverage product of comprises magnesium or a magnesium salt.

In one aspect the dietary supplement or food or beverage product comprises:
(a) Inulin;
(b) St. John's wort extract, Hyperforin, Ginkgo bilogoba extract, or Ginkgolide A or B, Rapamycin; and
(c) Citric acid.

In one aspect this dietary supplement or food or beverage product of further comprises magnesium or a magnesium salt.

In one aspect, the dietary supplement or food or beverage product is:
(a) yogurt;
(b) porridge;
(c) bread;
(d) baby food;
(e) a sports drink;
(f) an energy bar;
(g) chocolate.

In one aspect the dietary supplement is in the form of a tablet or capsule for oral ingestion.

It is thought that the dietary supplements of the invention increase lifespan or attenuate aging by activating the distinct pathways described herein.

This invention also provides a method of attenuating aging, of health maintenance, and/or treating or delaying the onset of, an age-related condition or disorder, the method comprising administering to the subject an effective amount of:
(a) one or more compounds that sustain the pharmacological activation of xenobiotic metabolism or induce fermentation by gut bacteria to produce substances that activate xenobiotic metabolism enzymes and/or stimulate xenobiotic excretion; and
(b) one or more chelators.

In one aspect the administration prolongs the lifespan of the subject relative to the lifespan of the subject in the absence of the administration.

In one aspect the administration treats or delays the onset of the age-related disease in the subject relative to the subject in the absence of the administration.

In one aspect of the method (a) is inulin.

In one aspect of the method (a) is an agonist of nuclear receptors that activate xenobiotic metabolism.

In one aspect of the method the agonist of nuclear receptors that activate xenobiotic metabolism is selected from the group consisting of constitutive androstane receptor (CAR) agonists, pregnane X receptor (PXR) agonists, or a peroxisome proliferator-activated receptor α (PPARα) agonist.

In one aspect of the method the agonist of nuclear receptors that activate xenobiotic metabolism is clofibrate.

In one aspect of the method (b) is: Lemon or lime extract, DTPA, EDTA, St. John's wort extract, Hyperforin, Ginkgo bilogoba extract, Ginkgolide A or B, vitamin C, Ascorbic acid 6-palmitate, Pantothenic acid (vitamin B-5), Niacinamide, Allicin (garlic), Lactobionate, Melatonin, Metformin, L-Dopa, extract Mucuna beans (Mucuna Dopa), L-Histidine, Quercetin, Curcumin, L-Glutamic acid, succinic acid, N-Acetil Cysteine, Green tea extract, Epigallocatechin-3-gallaye, Glutathione, Aspirin, Salicylate, Glycine, Resveratrol, Genistein, Garnosine, Rapamycin, Lipoic acid, or Taurine.

In one aspect of the method (b) is diethylenetriaminepentaacetic acid (DTPA).

In one aspect of the method the administration prolongs the lifespan of the subject more than the individual effect of the administration of either (a) or (b).

In one aspect of the method the administration prolongs the lifespan of the subject synergistically, i.e. more than the sum of the individual effect of the administration of (a) and (b).

In one aspect the method comprises administering to the subject an effective amount of one or more compound selected from the group consisting of:
(a) a COX inhibitor;
(b) an antiparasitic agent;
(c) an acetylcholinesterase inhibitor;
(d) an adenosine receptor antagonist;
(e) a selective estrogen receptor modulator.

In one aspect the method comprises administering to the subject an effective amount of a magnesium salt.

In one aspect the method comprises the magnesium salt is Magnesium hydroxide, Magnesium acetate, or magnesium chloride.

In one aspect the method comprises administering to the subject an effective amount of citric acid.

Each embodiment disclosed herein is contemplated as being applicable to each of the other disclosed embodiments. Thus, all combinations of the various elements described herein are within the scope of the invention.

Active Compounds

Preferable xenobiotic metabolism activator compounds include

Ginkgo biloba, specifically Ginkgolide A and B,
and St. John's Wort.

Preferable chelator compounds include:
Allicin (DS, extract of garlic)
Aminoguanidine,
Ascorbic acid 6-palmitate,
Aspirin,
Carnosine,
Curcumin,
Cysteine,
EDTA (DS)
Epigallocatechin-3-gallate,
extract Mucuna beans (Mucuna Dopa),
Genistein,
Glutathione
Glycine,
Green tea extract,
Guanidine,
Lactobionate,
L-Dopa (including Mucuna Dopa)

L-Glutamic acid,
L-Histidine (DS)
Melatonin,
Metformin
Methyl Salicylate,
Niacinamide,
Pantothenic acid (vitamin B-5),
Quercetin,
Resveratrol,
Salicylate,
Vitamin C.

Particularly preferable chelators are those which are shown to provide 10% or greater effect and include: Ascorbic Acid 6-Palmitate (Ascorbyl Palmitate), Citric Acid, D-Pantothenic Acid (Vitamin B-5), Melatonin, and Niacinamide (Vitamin B-3), and diethylenetriaminepentaacetic acid (DTPA).

Preferable magnesium compounds are those which are shown to provide 10% or greater effect and include: Magnesium Acetate, Magnesium Hydroxide and Manganese Sulfate.

Other preferable compounds which are those which are shown to provide 10% or greater effect and include: Hemicalcium and Peppermint Oil.

Xenobiotic metabolism activator compounds useful in the methods described herein, include, for example, compounds that act as agonists of nuclear receptors that activate or induce xenobiotic metabolism.

Suitable classes of agonist compounds include, but are not limited to, constitutive androstane receptor (CAR) agonists, pregnane X receptor (PXR) agonists and peroxisome proliferator-activated receptor a (PPARa) agonists, and any combination thereof.

Suitable examples of CAR agonists include, but are not limited to 6,7-dimethylesculetin, acetaminophen, artemisinin, atorvastatin, cerivastatin, CITCO ((6-(4-chlorophenyl)imidazo[2,1-b][1,3]thiazole-5-carbaldehyde-0-(3,4-dichlorobenzyl)oxime), fluvastatin, orphenadrine, phenobarbital, phenytoin, pravastatin, simvastatin, and combinations thereof.

Suitable examples of PXR agonists include, but are not limited to, 4-hydroxytamoxifen, androstenol, artemisinin, avasimibe, BK8644, bosentan, bromopropylate, butamifos, carbamazepine, cis-guggulsterone, clotrimazole, desmethoxyyangonin, dexamethasone, dihydromethysticin, dymuron, efavirenz, esprocarb, ethion, etoposide, flucythrinate, forskolin, hyperforin (hypericum perforatum extract or St John's wort), indanofan, isofenphos, isradipine, kava extract, lithocholic acid, lovastatin, meclizine, methadone, metlachlor, mevastatin, mifepristone, nicardipine, nifedipine, paclitaxel, PCN (pregnenolone-16a-carbonitrile), phenobarbital, piperophos, pretilachlor, pyributicarb, rifampicin, ritonavir, spironolactone, SR 12813, tamoxifen, thenylchlor, topiramate, topotecan, trans-guggulsterone, triadimefon, ursodeoxycholic acid, and combinations thereof.

Suitable examples of PPARα agonists include, but are not limited to, aleglitazar, arachidonic acid, bezafibrate, ciprofibrate, clinofibrate, clofibrate, clofibric acid, clofibride, CP 77 5146, eicosapentaenoic acid, etofibrate, fenofibrate, fenofibric acid, gemfibrozil, GW 7 64 7, linoleic acid, muraglitazar, nafenopin, oleic acid, oleylethanolamide, palmitic acid, palmitoleic acid, palmitoylethanolamide, pioglitazone, pirinixic acid, rivoglitazone, ronifibrate, rosiglitazone, saroglitazar, simfibrate, stearic acid, tesaglitazar, troglitazone, WY-14643, and combinations thereof.

Suitable examples of cardiac glycosides include, but are not limited to, acetyldigitoxin, acetyldigoxin, arenobufagin, bufotalin, cinobufagin, cymarm, deslanoside, Digitalis leaves, digitoxin, digoxin, gitoformate, K-strophanthin, lanatoside C, marinobufagin, metildigoxin, ouabain, peruvoside, proscillaridin (e.g., proscillaridin A), scilliroside, and combinations thereof.

Suitable examples of COX inhibitors include, but are not limited to, aspirin, nonsteroidal anti-inflammatory drugs (NSAIDs) (such as ibuprofen, piroxicam, mefenamic acid, diclofenac, flurbiprofen, and indomethacin), COX-2 inhibitors (such as celecoxib), and combinations thereof.

Suitable examples of antiparasitic agents include, but are not limited to, mebendazole, pyrantel pamoate, thiabendazole, diethylcarbamazine, ivermectin, niclosamide, praziquantel, albendazole, praziquantel, rifampin, amphotericin B, melarsoprol, eflornithine, metronidazole, tinidazole, miltefosine, and combinations thereof.

Suitable examples of acetylcholinesterase inhibitors include, but are not limited to, donepezil, galantamine, caffeine, delta9-tetrahydrocannabinol (THC), physostigmine, neostigmine, pyridostigmine, ambenonium, demecarium, rivastigmine, tacrine, edrophonium, huperzine A, ladostigil, ungeremine, lactucopicrin, and combinations thereof.

Suitable examples of adenosine receptor antagonists include, but are not limited to, caffeine, 8-cyclopentyl-1,3-dipropylxanthine (DPCPX), cyclopentyltheophylline (CPT), istradefylline, SCH-58261, dyphylline, theophylline, theobromine, proxyphylline, pentoxiphylline, etofylline, aminophylline, dimenhydrinate, and combinations thereof.

Suitable examples of chelators include, but are not limited to, 2,3-dimercapto-lpropanesulfonic acid (DMPS), alpha lipoic acid, BAPTA, citric acid, deferasirox, deferiprone, deferoxamine (DFO), dimercaprol (BAL), dimercaptosuccinic acid (DMSA), ethylene glycol tetraacetic acid (EGTA), ethylenediaminetetraacetic acid (EDTA), penicillamine, pentetic acid (DTPA), Prussian blue, succinic acid, tartaric acid, triethylenetetramine (TETA), N-acetyl-L-cysteine, aspartic acid, histidine, glutamic acid, glutathione, etindronic acid, methionine, selenomethionine, taurine, alendronic acid, clodronic acid, tiopronin, diethyldithiocarbamate, and combinations thereof.

Additional inducers of xenobiotic metabolism include, but are not limited to, 2-naphthoflavone, 3-methylcholanthrene, dioxin, metyrapone, decitabine, trichostatin A, hydroxymethylpyrene, indolo [3,2-b] carbazole, phenethylisothiocyanate, isothiocyanatomethylbenzene, sulforaphane, coumestrol, testosterone, dihydrotestosterone, indole-3-carbinol, 3-nitrobenzanthrone, 2-(4-amino-3-methylphenyl)-5-fluorobenzothiazole, primaquine, iprodione, ketoconazole, deltamethrin, omeprazole, pentachlorophenol, fipronil, sulindac, 3-aminobenzanthrone, 6-nitrochrysene, ltraconazole, Enilconazole (imazalil), 2-[2-(acetylamina)-4-(diallylamina)-5-methoxyphenyl]-5-amino-7-bromo-4-chloro-2H-benzotriazole (PTBA-8), 9-hydroxy-5,6-dimethyl-N-[2-(dimethylamino)ethyl]-6H-pyrido(4,3-b)-carbazole-1-carboxamide, carbaryl, 6-formylindolo[3,2-b]carbazole, 2-[2-(acetylamino)-4-(diethylamino)-5-methoxypheny]-5-amino-7-bromo-4-chloro-2H-benzotriazole (PB TA-7), chlorpyrifos, sulindac sulfone, fluconazole, permethrin, ascorbigen, DEET (N,N-diethyl-metatoluamide), clevidipine, emodin, 4-biphenylamine, nevirapine, efavirenz, chlorpyrifos oxon, ibrolipim, isoniazid, ethanol, tretinoin, fandosentan potassium, modafinil, trazodone, trimeprazine, etoposide, doxorubicin, rifabutin, alpha-naphthoflavone, progesterone, ethambutol, benzil, 1-methylphenanthrene, olopatadine, ethionamide, quercetin, 4-hydroxynonenal, oltipraz, butanoate, resveratrol, paraquat, alpha lipoic acid, carnoslc acid, camosol, oxaliplatin, paclitaxel, nicotinamide, azathioprine, eugenol, chlorophyllin, 2-tert-butylhydroquinone, hydrocortisone, procainamide, corticosterone, medroxyprogesterone 17-acetate, dopamine, 4-nitrophenol, bilirubin, glycyrrhizic acid, nanngenm, saccharolactone, isopropyl thiogalactoside, naphthyl glucuronide, epigallocatechin gallate, imipramine, serotonin, nicotine, cotinine, propylpyrazoletriol, genistein, pyrazole, ITE 2-(1H-indol-3-ylcarbonyl)-4-thiazolecarboxylic acid methyl ester), MeBIO ((2'Z,3'E)-6-bromo-1-methylindirubin-3'-oxime), pifithrin-a, and combinations thereof.

Routes of Administration

Any route of administration may be selected for use in the methods described herein. For instance, the route of administration may be selected from oral, nasal, buccal, rectal, vaginal, ophthalmic, subcutaneous, intramuscular, intraperitoneal, intravenous, intraarterial, intratumoral, spinal, intrathecal, intra-articular, intra-arterial, sub-arachnoid, sublingual, oral mucosa!, pulmonary, bronchial, lymphatic, intra-uterine, subcutaneous, intratumor, integrated on an implantable device, intradural, intracortical, dermal, epidermal, transdermal, vaginal, rectal, ocular (for examples through the conjunctiva), intraocular, uretal, and parenteral. A preferred route of administration is oral.

Dosages

The actual dosage amount of the active compound(s) administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active compound(s) in a composition and appropriate dose(s) for the individual subject.

In one embodiment, a human subject is administered the daily dose of from about 0.01 mg/kg to about 1000 mg/kg of the active compound(s). Preferably, the dosage level will be about 0.1 to about 250 mg/kg per day, more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be about 0.05 to 0.5, about 0.5 to 5 or about 5 to 50 mg/kg per day. For oral administration, the compositions are preferably provided in the form of tablets containing 0.1 to 1000 mg of the active compound(s), for example, about 0.1, 0.5, 1, 5, 10, 15, 20, 25, 50, 75, 100, 125, 150, 175, 200, 225, 250, 275, 300, 350, 400, 450, 500, 550, 600, 650, 700, 750, 800, 850, 900, 950 or about 1000 mg of the active compound(s).

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day (once daily), every two days, every three days, every four days, every five days, every six days, a weekly basis, a monthly basis or any set number of days or weeks there-between.

In certain embodiments, the compounds described herein can be administered over an extended period of time, for example, for at least 1, at least 2, at least 6, at least 12, at least 18 or at least 24 months (or, for example, for 18 months, 2 years, 21 h years, or for 3 years).

In one embodiment, the methods described herein do not involve coadministration of estrogen receptor agonists (including endogenous estrogens, such as 17-estradiol and estrone, and synthetic estrogens, such as diethylstilbestrol and hexestrol).

Pharmaceutical Compositions

The compounds described herein may be administered (e.g., orally) in the form of a solid or liquid dosage form. In both, the compounds may be coated in a material to protect them from the action of acids and other natural conditions which may inactivate the compounds. The compounds may be formulated as aqueous solutions, liquid dispersions, (ingestible) tablets, buccal tablets, troches, capsules, elixirs, powders, granules, ointments, adhesive skin patches, sprays, suspensions, syrups, and wafers. The dosage forms may include pharmaceutically acceptable excipients, diluents, and/or carriers known in the art, such as binders, disintegrating agents, emulsifiers, lubricants, flavorants, antioxidants, and preservatives. Liquid dosage forms may include diluents such as saline or an aqueous buffer.

The active compounds can be administered as foods, food additives, edible soluble films, drinks, medicinal agents, and feeds for domestic and wild animals. The drinks may be non-alcohol drinks or alcohol drinks. Examples of non-alcohol drinks include carbonated drinks, non-carbonated drinks (such as fruit juice, and nectar), soft drinks, sports drinks, tea, coffee, and hot chocolate. The alcohol drinks may be in the form of, for example, beer, low-malt beer, third-category beer, sake, umeshu, wine, champagne, liqueur, chuhai, or medicated liquor.

For use as a food material or food additive (e.g., human food or animal food, such as dog or cat food or feed for poultry, cows, or pigs), the active compound may be in the form of, for example, a tablet, a capsule formulation, a solid agent (such as a powder and a granule) dissolved in drinks, a semi-solid such as jelly, a liquid (such as drinking water), and a high-concentration solution diluted before use. Optional components, such as vitamins, carbohydrates, dyes, and flavoring agents commonly added to food may be appropriately mixed. The food may be given in any form, including a liquid and a solid.

Dietary Supplements

The dietary supplement may also comprise one or more compounds known to those of ordinary skill to be useful in dietary supplements, including, but not limited to, vitamins, minerals (e.g., magnesium), fatty acids, antioxidants, amino acids, palatants and nutraceutical additives, and any combination thereof. See the National Institute of Health Dietary Supplement Database: http://www.dsld.nlm.nih.gov/dsld. For example, the dietary supplement may also include one or more calcium-containing materials such as calcium carbonate, stannol esters, hydroxycitric acid, vitamins, minerals, herbals, spices and mixtures thereof. Examples of vitamins that are available as additional ingredients include, but are not limited to, vitamin A (retinal), vitamin D (cholecalciferol), vitamin E group (alpha-tocopherol and other tocopherols), vitamin K group (phylloquinones and menaquinones), thiamine (vitamin B1), riboflavin (vitamin B2), niacin, vitamin B6 group, folic acid, vitamin B12 (cobalamins), biotin, vitamin C (ascorbic acid), and mixtures thereof. The amount of vitamin or vitamins present in the final product is dependent on the particular vitamin. Examples of minerals that are available as additional ingredients include, but are not limited to, calcium, magnesium, phosphorus, iron, zinc, iodine, selenium, potassium, copper, manganese, molybdenum and mixtures thereof. As is the case with vitamins, the amount of mineral or minerals present in the dietary supplement is dependent on the particular mineral.

Subject

The subject is a mammal, such as a human, or, for example, a domestic or wild animal, such as a chicken, quail, ostrich, horse, bird, dog, cat, cow or pig. Preferably, the subject is a human, such as a male or female adult. For example, the subject may be an adult who is between 18 and 30 years old, between 30 and 40 years old, between 40 and 50 years old, between 50 and 60 years old, between 60 and 70 years old, and between 70 and 80 years old.

Reference to Other Publications or References and to the Experimental Details

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1

In order to improve our understanding of the underlying biochemical pathways that determine longevity, the inventors conducted a large-scale screen in mice, testing the effects of 1033 well-defined pharmacological compounds on lifespan. The majority of compounds included drugs currently used in medicine and drug-like molecules, with wide range of targets that span the entire pharmacological space.

The compounds were clustered into 62 drug classes based on their mechanism of action or cellular target. Screening a wide range of known compounds could potentially resolve two challenges. First, to analyze how distinct drug classes with common mechanisms of action affect aging in mammals. Second, to determine with no bias or predispositions which of the current pharmacological drugs can extend lifespan.

In this study, the inventors used a strain of long-lived B6C3F1 hybrid mice (C57BL/6J ♀ ×C3H/HeJ ♂) with well-characterized aging dynamics (Lipman 1999, Turturro, 1999). The study design was shaped to test a large number of compounds, yet still identify individual compounds that significantly extend lifespan by at least 15%. Each treatment group included 15 female mice per compound, while 335 females were used as controls. Three additional control groups included 60 female mice on dietary restriction (60% ad libitum), 60 female mice on a purified diet, and 60 male mice as gender control. Each compound treatment and diet intervention were administered to mice starting at 5 months of age, and continued throughout their lifespan. The primary endpoint was mouse mortality, from which we calculated mean lifespan, maximal lifespan, and the onset of morbidity for each experimental group. To calculate the statistical significance, the mean lifespan, maximal lifespan, and the onset of morbidity for each individual compound and drug class were compared to the lifespan distribution of untreated mice. This comparison yielded raw p-values, which were then adjusted to control for the false discovery rate (i.e. for the fact that >1000 compounds were tested in the screen) (Benjamini, 1995).

Figure 1C:
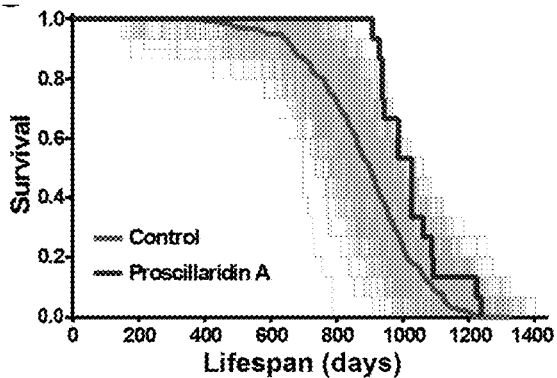
FIG. 1C—Proscillaridin A extended mouse onset of morbidity by 39.9% (p=5×10−3) and mean lifespan by 16.4% (p=5×10−2). The grey plots in the background represent the survival curves of all compounds used in the screen.
Figure 1D:
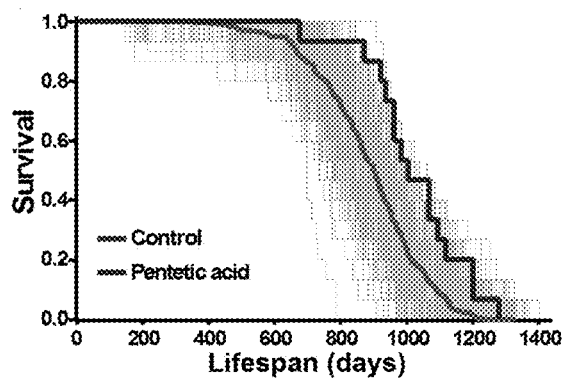
FIG. 1D—Pentetic acid extended mean lifespan by 16.1% (p=5.5×10−2). The grey plots in the background represent the survival curves of all compounds used in the screen.
Figure 1E:
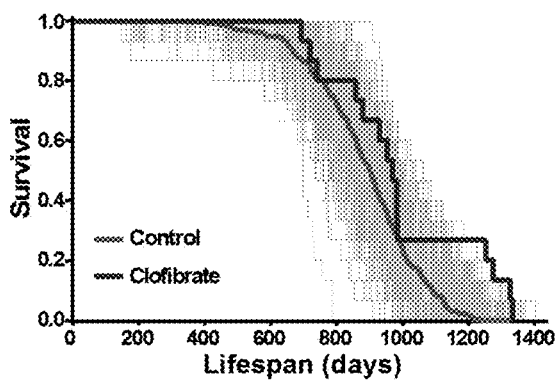
FIG. 1E—Clofibrate extended maximal lifespan by 20.9% (p=1.4×10−2). The grey plots in the background represent the survival curves of all compounds used in the screen.
Figure 1F:
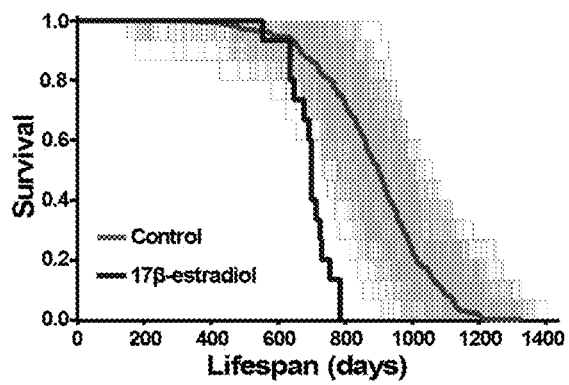
FIG. 1F—The compound that most significantly reduced mouse lifespan was natural estrogen 17β-estradiol, which reduced mean lifespan by 21% (P=2×10−2). The grey plots in the background represent the survival curves of all compounds used in the screen.
Figure 2:
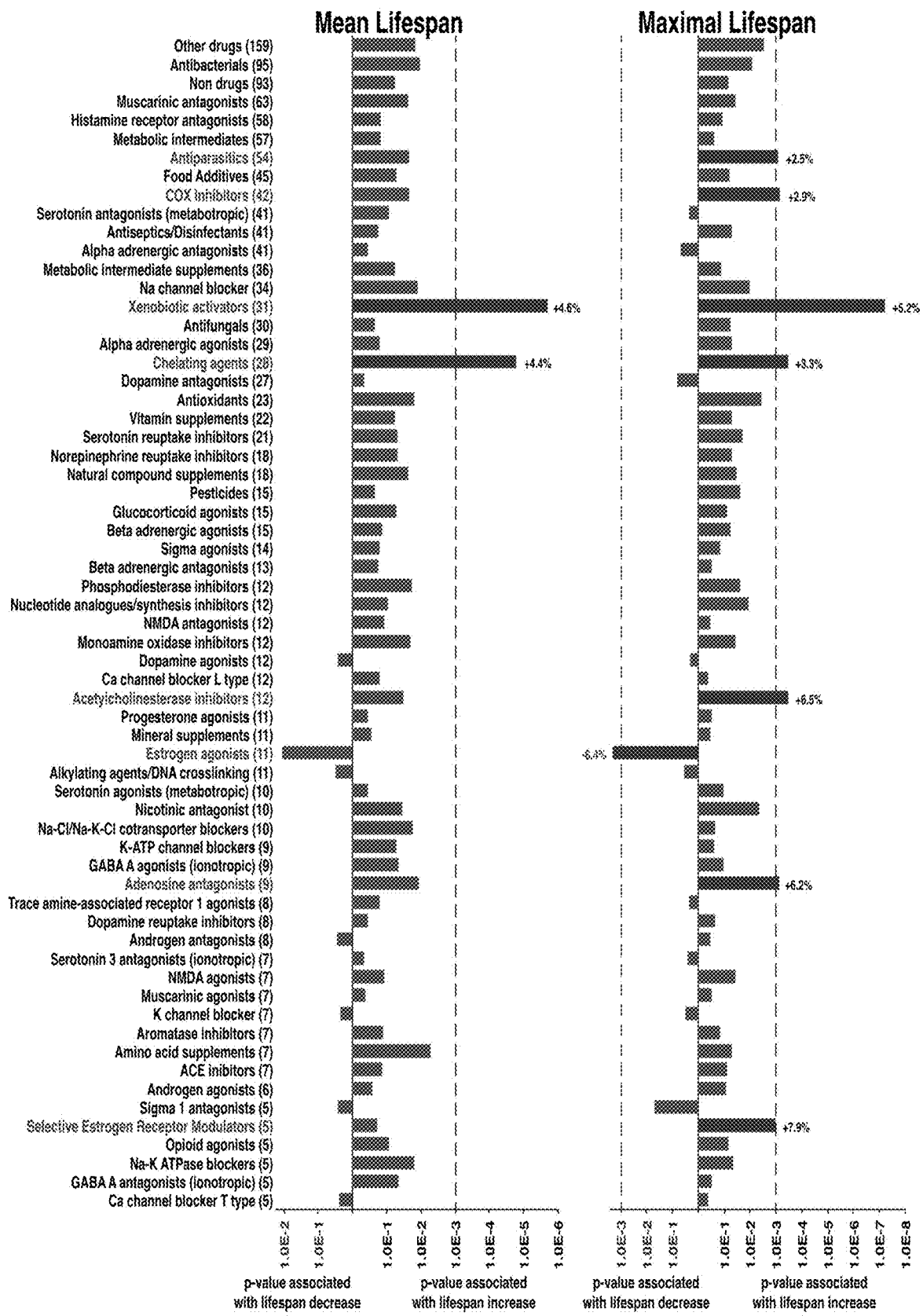
FIG. 2—The values depicted next to each bar represent actual percent change in mean or maximal lifespan relative to controls. The numbers in the parentheses following the class name represents the number of compounds within the respective class. Several drug classes extended mean and maximal mouse lifespan, with most significant effects achieved by activators of xenobiotic metabolism and chelating agents. The only drug class that significantly decreased lifespan contained agonists of the estrogen receptor. Maximal lifespan was calculated as the average lifespan of the 20% longest-lived mice.
Figure 3:
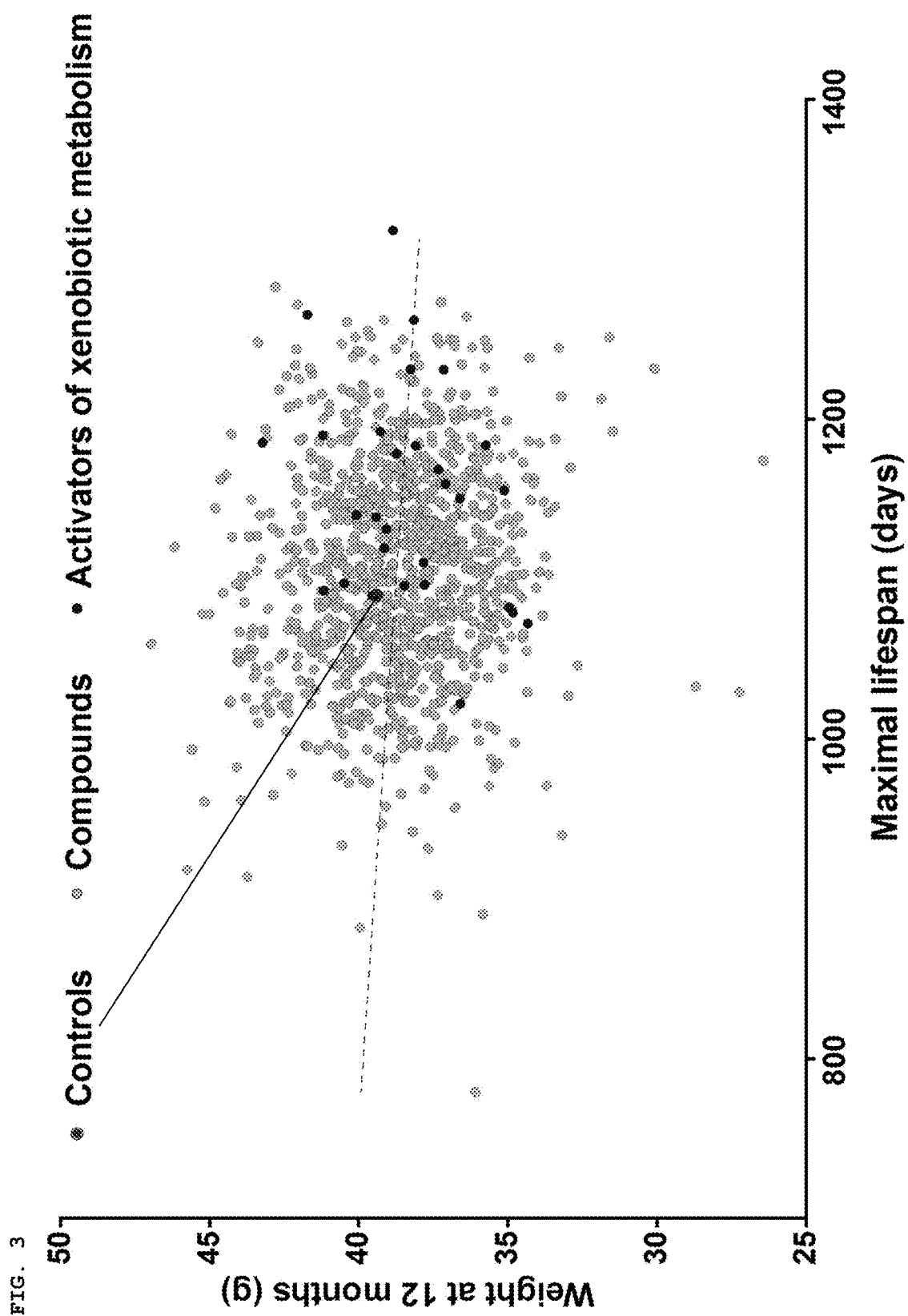
FIG. 3. A global view of the screen results highlighting the effects of individual activators of xenobiotic metabolism (dark blue) on maximal lifespan. Activators of xenobiotic metabolism did not exhibit an altered weight distribution relative to other compounds, indicating that their lifespan-extending effects were not due to voluntary caloric restriction. Overall, mouse weight exhibited a slight but statistically significant negative correlation with lifespan at 5 months ($p=7\times10-3$)—i.e. before the start of compound dosing—as well as at 6 months ($p=1\times10-2$) and 12 months ($p=4\times10-3$), consistent with results reported by Yuan et al.
Figure 4:
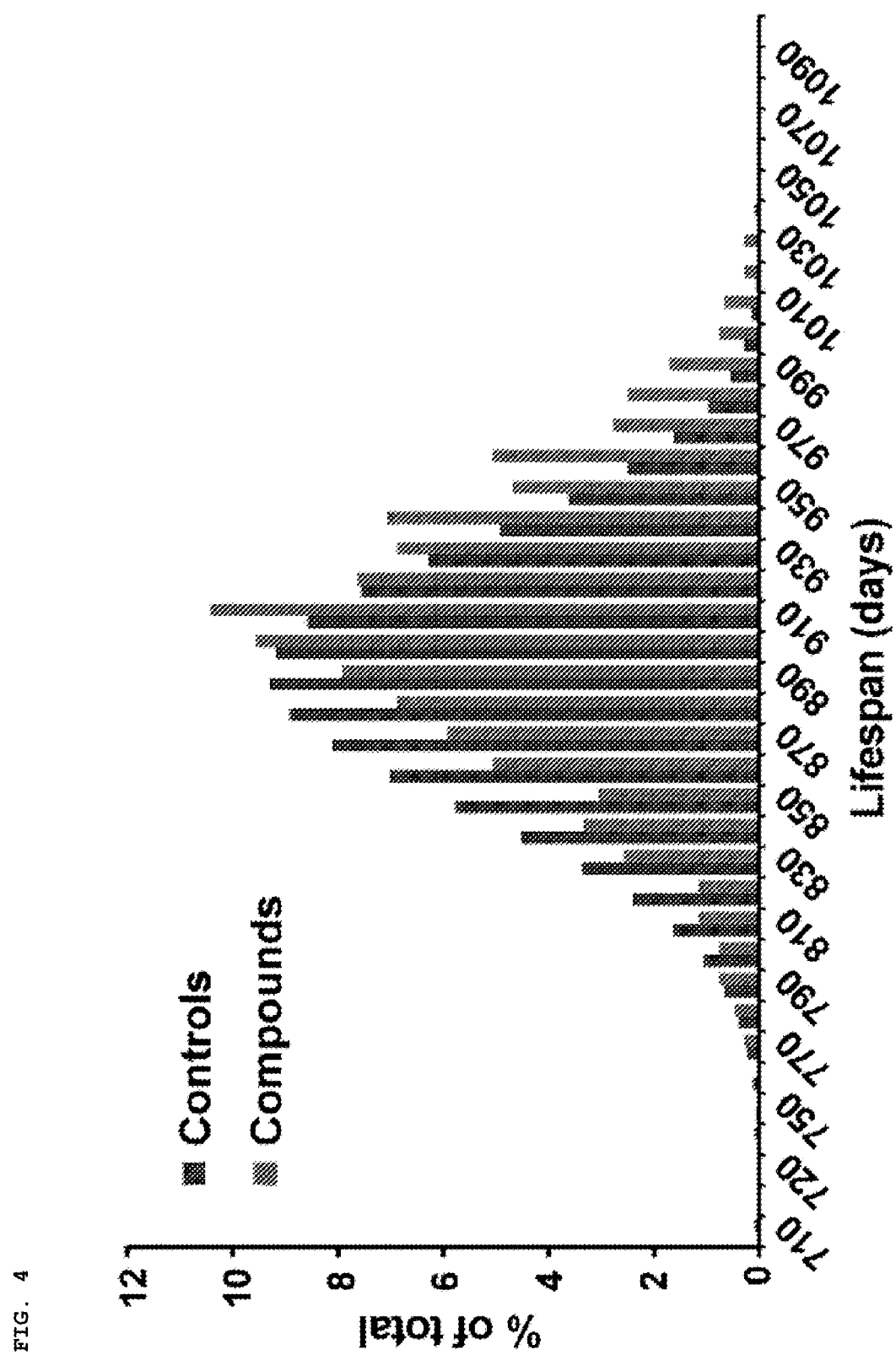
FIG. 4 is a histogram comparing the lifespan of the control and compound treated B6C3F1/J mice described in Example 1.
Figure 5:
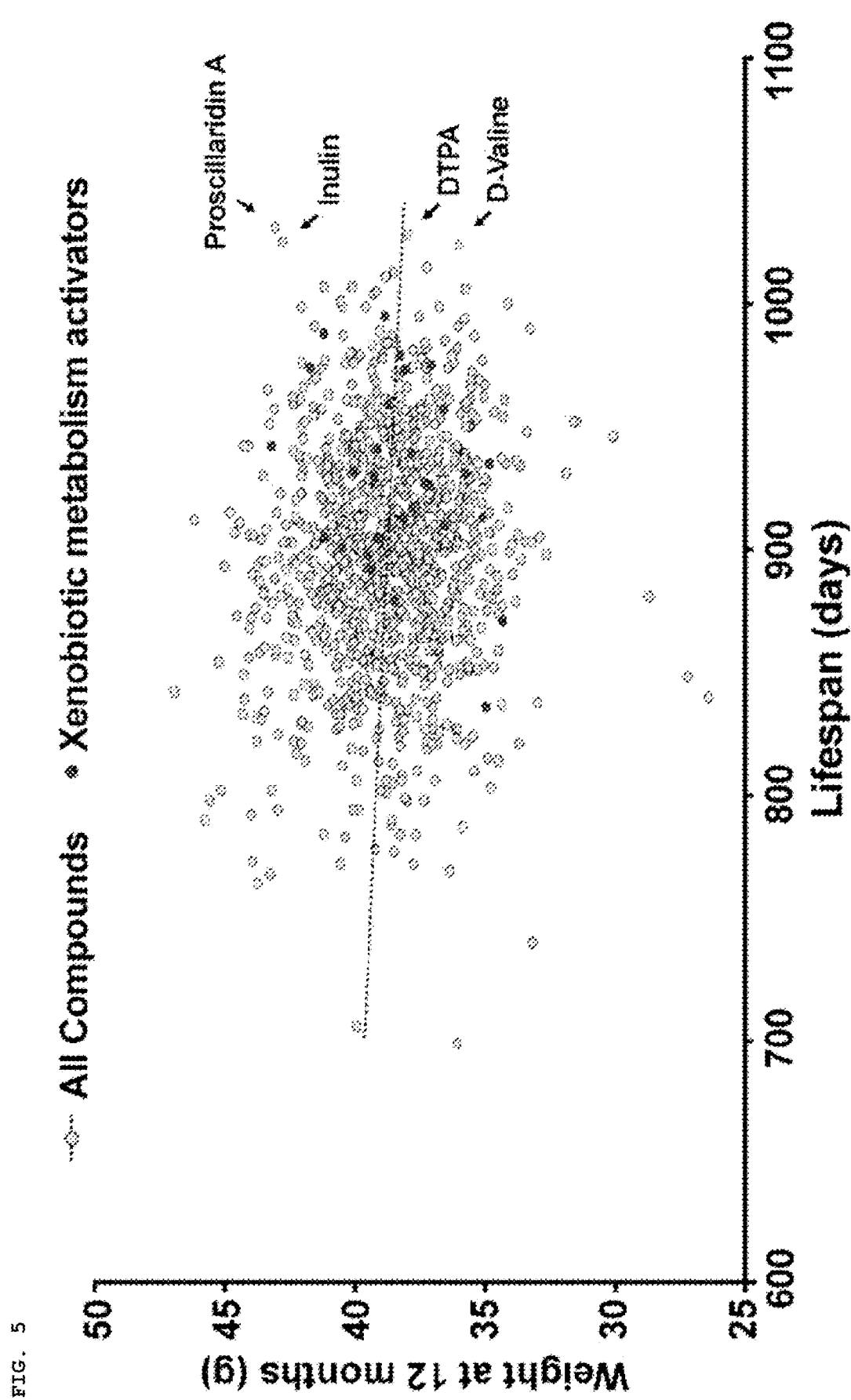
FIG. 5 depicts a global view of the screening results, highlighting the effects of individual activators of xenobiotic metabolism.
Figure 6A:
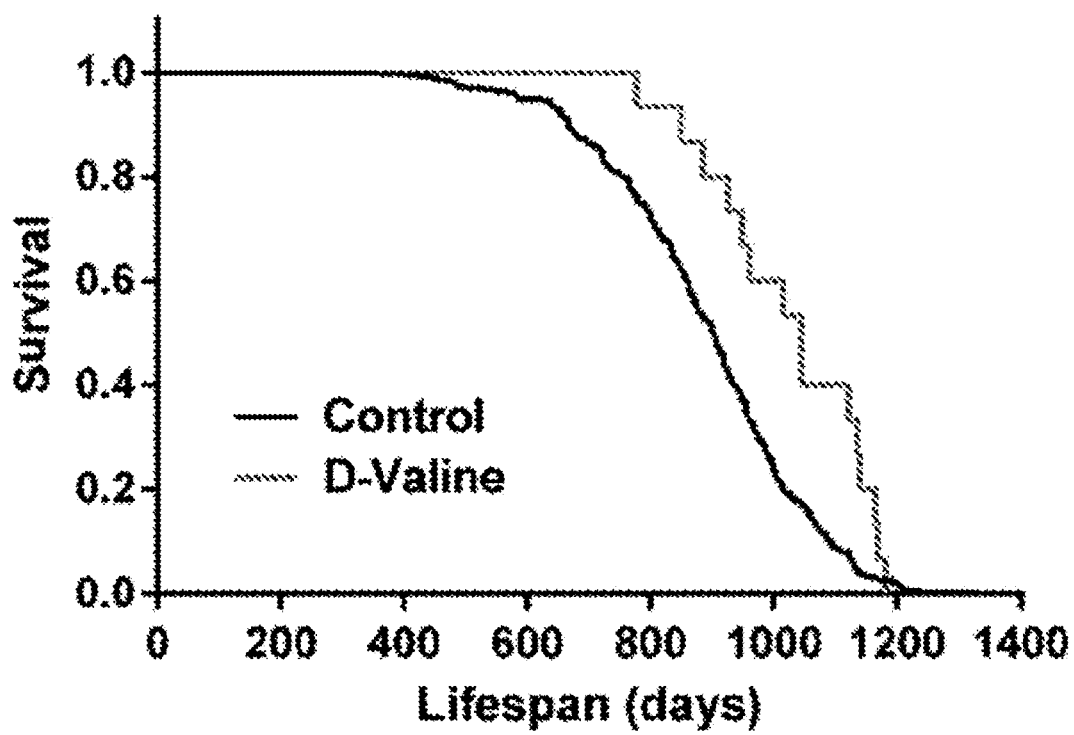
FIG. 6A depicts the effect of D-valine on the lifespan of B6C3F1/J mice.
Figure 6B:
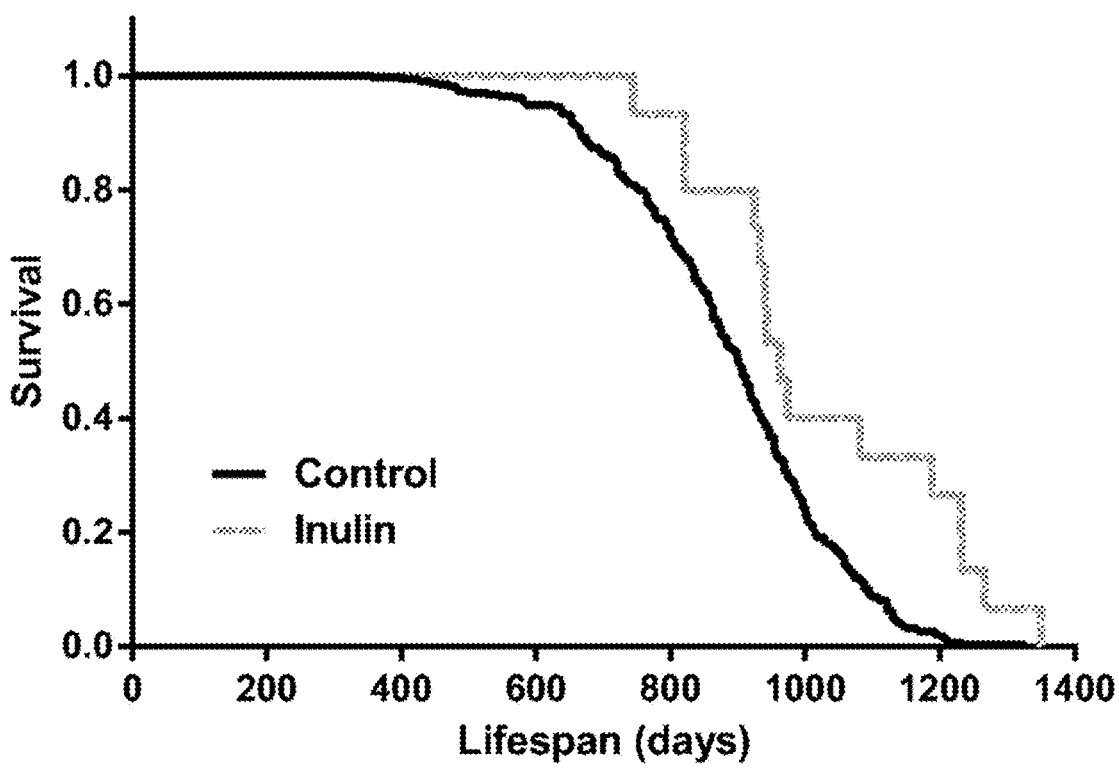
FIG. 6B depicts the effect of inulin on the lifespan of B6C3F1/J mice.

Inventors identified 2 out of 62 drug classes in total that exhibited by far the most significant extension of lifespan—xenobiotic metabolism activators and chelating agents (FIG. 2). In addition, the inventors identified four individual compounds that significantly extended mean and/or maximal lifespan—Clofibrate, Pentetic Acid, Inulin, and Proscillaridin A. Finally, only one compound significantly shortened lifespan-1β-estradiol (mean lifespan by 21%; FIG. 1F).

Xenobiotic metabolism activators exhibited the most significant extension of both mean, and maximal lifespan ($p=2.0\times10-6$ and $p=6.2\times10-8$ respectively). These comprised molecules that are strong agonists of nuclear receptors constitutive androstane receptor (CAR), pregnane X receptor (PXR), and peroxisome proliferator-activated receptor alpha (PPARα), which together are known to induce xenobiotic metabolism enzymes.

Xenobiotic metabolism has been previously implicated in longevity in diverse organisms by studies demonstrating that activation of xenobiotic metabolism and increased xenobiotic resistance are common to best-studied and most robust means of lifespan extension (Amador-Noguez 2007, Gems 2005, McElwee 2004, Steinbaugh 2012, Zimniak 2008). For example, it was demonstrated by gene expression and metabolomic studies in rodents that dietary restriction upregulates the expression of many detoxification enzymes (Steinbaugh 2012, Wen 2013). It was also demonstrated in various long-lived animal models, including Caernohabditis elegans daf-2 mutants and dwarf mouse strains, that lifespan extension is associated with upregulated expression of detoxification enzymes (Amador-Noguez 2007, McElwee 2005, Steinbaugh 2012, McElwee 2007). Finally, the best-studied example of pharmacological extension of mouse lifespan using rapamycin is also characterized by upregulated expression of xenobiotic metabolism genes (Steinbaugh 2012). Here, inventors present evidence that direct pharmacological activation of xenobiotic metabolism can be sufficient to extend mammalian lifespan.

Xenobiotic metabolism is a highly regulated process whose major function is biotransformation and elimination from the body of lipophilic toxic molecules that are normally generated as products of metabolism (a.k.a. endobiotics), or absorbed from the environment (a.k.a. xenobiotics) (Omiecinski 2011). The function of xenobiotic metabolism is carried out by a battery of detoxification enzymes that are categorized into several distinct phases, including phase I and phase II enzymes. Phase I enzymes, such as cytochrome P450s, catalyze biotransformation reactions (e.g. hydroxylation) to functionalize the chemically inert xenobiotic molecules, while phase II enzymes (including UDP-glucuronosyltransferases and glutathione S-transferases) catalyze covalent attachment of polar side groups to functionalized xenobiotics, increasing their solubility and promoting their excretion. Other factors involved in xenobiotic metabolism are drug transporters that promote xenobiotic excretion.

The largest extension of maximal lifespan by an individual compound was exhibited by clofibrate (21%; FIG. 1F). Interestingly, clofibrate is already known as a strong agonist of PPARα and has classically been used to activate xenobiotic metabolism (Guo 2007). Recently it has also been demonstrated that clofibrate extends lifespan in C.

*elegans*, and this effect is dependent on a *C. elegans* homolog of mammalian PPARα (Brandstadt 2013). Therefore, in accord with previous findings, the lifespan extending effect of clofibrate may be the direct result of activation of cellular detoxification through PPARα activation.

Chelating agents are the second drug class to induce significant extension of mean and maximal lifespans ($p=1.6\times10-5$ and $p=3.4\times10-4$ respectively). Furthermore, pentetic acid (diethylene triamene pentaacetic acid), a strong chelator was one of the top individual life extending compounds, extending mean lifespan by 16% (FIG. 1D; $p=5\times10-2$). Interestingly, it was also demonstrated recently that treatment with chelating agents could extend lifespan in *C. elegans* (Klang 2014). Pentetic acid is an EDTA-like strong chelator that is currently under development as an oral drug to remove radioactive ions.

The canonical function of chelators in organisms is to facilitate the removal of metal ions such as lead, arsenic, cadmium, mercury, iron, copper, etc. Transition metals, such as iron and copper, are known to catalyze the nonspecific formation of advanced glycation end-products (AGEs). Nonenzymatic and nonspecific glycoation of proteins, nucleic acids, and lipids (ALEs) has been linked to cross-linking of molecules, cell senescence and stiffening of tissues at old age. In addition to tissue damage, AGEs are also sensed by RAGE receptor that induces chronic inflammation. Interestingly it was demonstrated that all currently known agents that prevent formation of AGEs act as chelators, suggesting that chelation of transition metal ions can extend lifespan through prevention of AGE formation.

Chelation agents can also protect from heavy metal poisoning. The accumulation of these metals at low levels in organisms can exert severe toxicities and pathologies, in addition to the heavy acute toxicities they can cause in the event of poisoning (Sears 2013, Apostoli 2006). Heavy metals exert their direct toxic effects by binding to tissues, causing DNA damage, binding to proteins and interfering with functions of zinc and magnesium, immunosensitization, and immunosuppression (Sears 2013, Apostoli 2006). Heavy metals can also generate reactive oxygen species and oxidative stress, mainly by catalyzing the formation of hydroxyl radicals. Our results suggest that chelation therapy can slow down aging through one or more mechanisms.

Inventors also identified five drug classes that extended only maximal lifespan with marginal statistical significance, consisting of acetylcholinesterase inhibitors, adenosine receptor antagonists, antiparasitic agents, cyclooxygenase (COX) inhibitors, and selective estrogen receptor modulators ($p\sim1\times10-3$).

In addition to clofibrate and pentetic acid, another two compounds significantly extended lifespan. First, Proscillaridin A, a cardiac glycoside, extended mean lifespan by 16% and onset of morbidity by 40% (FIG. 1C). Second, inulin, a dietary fiber, extended mean lifespan by 16% and maximal lifespan by 18%. Proscillaridin A has not been previously implicated in longevity and thus represents novel anti-aging pharmacological agent. On the other hand, Inulin is exceptionally interesting because it may also act by activating xenobiotic metabolism. Inulin is a soluble fiber that cannot be broken down by mammalian cells; however, it can be metabolized by certain kinds of beneficial gut bacteria, helping to promote a healthy gut flora (Macfarlane 2008). Inulin fermentation by gut bacteria produces substances that induce xenobiotic metabolism enzymes and stimulate xenobiotic excretion (Buddington 2002, Sauer 2007), suggesting that inulin may extend lifespan by activating xenobiotic metabolism. The role of gut flora in aging is also supported by a recent study demonstrating the restructuring of the gut microbiome during aging in mice, and its modulation by caloric restriction (Zhang 2013).

In addition to the compounds listed above, the screen identified over 50 compounds that extended mean mouse lifespan by >10%. This number is over three-fold higher than that expected by chance, indicating that these compounds present a strong pool of candidates for future longevity studies. Thus, the screen identified a number of drugs whose effectiveness in extending longevity could potentially match that of rapamycin (Harrison 2009, Miller 2011).

Surprisingly, clustering all compounds in the screen and comparing them to controls revealed that on average compound treatment correlated with increased lifespan (+1.5%, $p<10-10$; FIG. S2). This phenomenon is reminiscent of hormesis, i.e. when low-dose treatment with toxic compounds can exhibit beneficial effect (Gems 2008). In fact, it was also proposed the hormetic effect is mediated by activation of xenobiotic metabolism (Gems 2008). Naturally the majority of our tested compounds are themselves substrates of xenobiotic metabolism. It is possible that the slight lifespan extension by majority of compounds is also mediated through activation of xenobiotic metabolism. In addition many drugs are known to act as chelating agents (Nagai 2012). Even such drugs as aspirin and metformin can act as chelating agents. Therefore the slight extention of lifespan by majority of compounds can in some cases be explained by their chelating activity.

The only drug class that significantly shortened mouse lifespan comprised estrogen receptor (ER) agonists (maximal $p=1.5\times10-5$; mean $p=9.0\times10-3$; FIG. 2), including endogenous estrogens 17β-estradiol and estrone, as well as synthetic estrogens, e.g. diethylstilbestrol and hexestrol. Furthermore, the only individual compound to significantly shorten lifespan was 17β-estradiol, shortening mean lifespan by 21% (FIG. 1F; $p=2\times10-2$). It is worth noting that drugs classified as selective estrogen receptor modulators (SERMs) that antagonize ER signaling as a group extended maximal lifespan ($p=1\times10-3$; FIG. 2), consistent with the hypothesis that hyper-activation of ER signaling shortens lifespan.

These results are consistent with known roles of estrogen signaling in reproduction and growth—processes known to antagonize longevity (Bartke 2013). In particular, estrogen signaling promotes secretion of growth hormone (GH) and functionally interacts with the IGF-1 pathway (Hewitt 2010, Kahlert 2000, Hamelers 2003), thus directly stimulating specific pro-growth pathways whose inactivation prolongs lifespan in several experimental model systems (Bartke 2013). Lastly, the discovery that mammalian lifespan can be extended by activators of xenobiotic metabolism and chelators and shortened by estrogen and estrogen-like compounds is consistent with current evolutionary theories of aging, where it is postulated that the lifespan of a species is determined by its choice of allotment of resources to competing, energetically costly evolutionary strategies: detoxification and maintenance vs. reproduction and growth (Gems 2005, Zimniak 2008, Bartke 2013, Gems 2013, Kirkwood 1977, Kirkwood 2000).

In conclusion, by conducting an unbiased, large-scale screen the inventors were able to elucidate a comprehensive map of pharmacological effects on mammalian longevity. Most importantly, the results indicate that mammalian lifespan can be extended through pharmacological activation of xenobiotic metabolism or treatment with chelating agents. This suggests that xenobiotic- and endobiotic-mediated damage, and damage caused by heavy metal ions, are major contributors to aging and are determinants of lifespan. It is also noteworthy that xenobiotic metabolism and removal of heavy metals through chelation are both detoxification systems. We hypothesize that nuclear receptors responsible for regulation of xenobiotic metabolism epitomize an ideal pharmacological target for anti-aging drugs that could be exploited in the near future for the development of lifespan extending compounds for humans. In addition, combining xenobiotic metabolism activators with chelation therapy should produce synergistic effects.

The inventors also identified inulin—a dietary supplement, which exhibited lifespan extension likely through indirect activation of xenobiotic metabolism. Inulin is already widely used as a prebiotic and is known for its beneficial effects to human health (Macfarlane 2008, Tuohy 2007). This means that inulin could be tested for effects on human aging immediately. If the effect of inulin on mouse lifespan is recapitulated in humans, the consequences for human health are expected to be unprecedented, surpassing the eradication of multiple age-related disorders (Goldman 2013).

CONCLUSION

The inventors found that 2 drug classes exhibited significant mean and maximal lifespan extension, consisting xenobiotic metabolism activators and chelating agents. The results suggest that xenobiotic- and endobiotic-mediated damage, and damage caused by metal ions, constitute the major determinants of mammalian longevity. In the case of chelating agents, the most likely explanation of their lifespan extending effect is prevention of formation of Advanced Glycation End products (AGEs) due to chelation of transition metal ions such as $Fe^{2+}$ and $Cu^{2+}$. In addition, the inventors identified individual compounds, including an activator of xenobiotic metabolism, a chelating agent, and a common dietary supplement that significantly extended lifespan.

This study demonstrates novel anti-aging strategies potentially applicable to humans.

Example 2

Figure 7A:
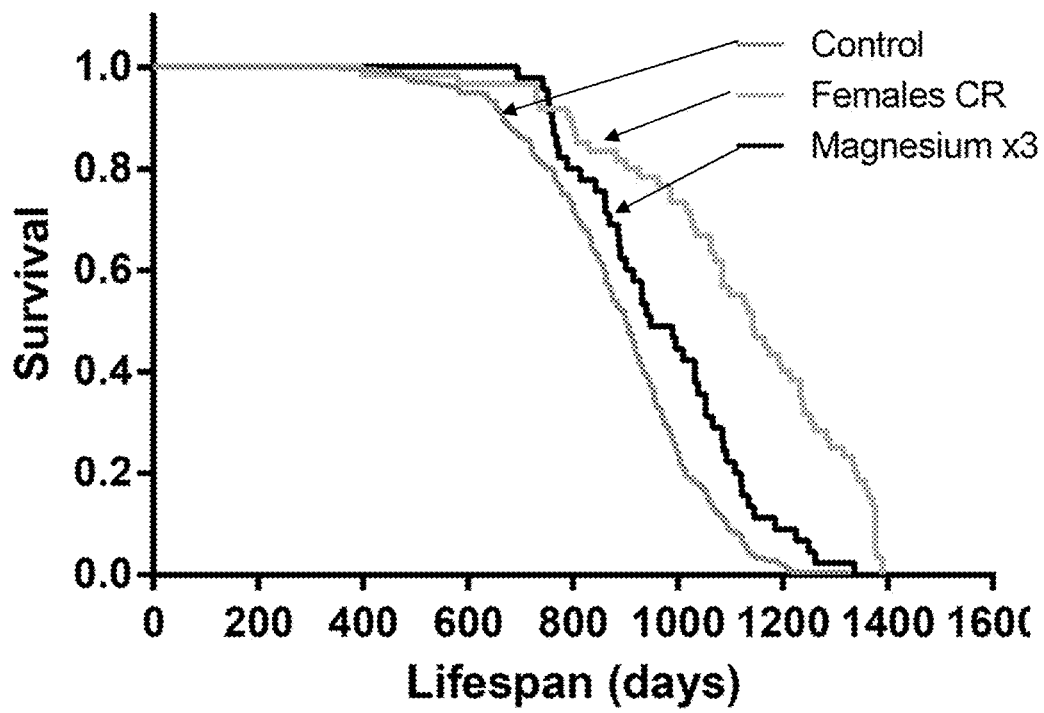
FIG. 7A depicts the effect of Magnesium ×3 on the lifespan of B6C3F1/J mice.
Figure 7B:
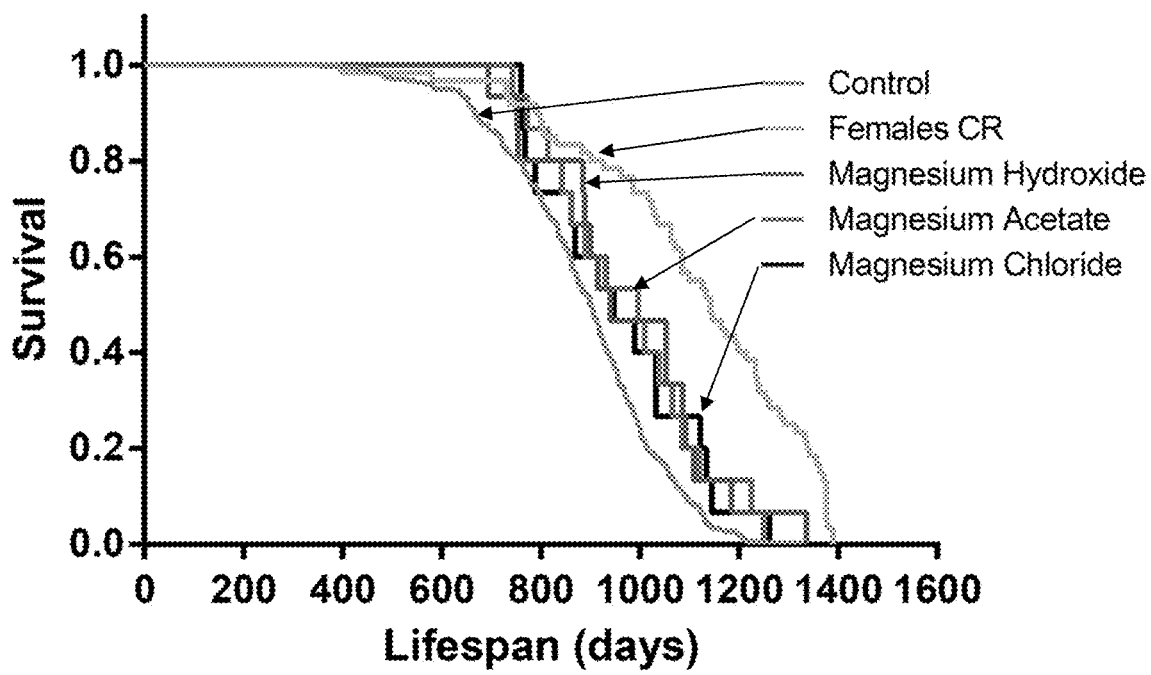
FIG. 7B depicts the effect of Magnesium Hydroxide, Magnesium Acetate and Magnesium Chloride on the lifespan of B6C3F1/J mice.
Figure 7C:
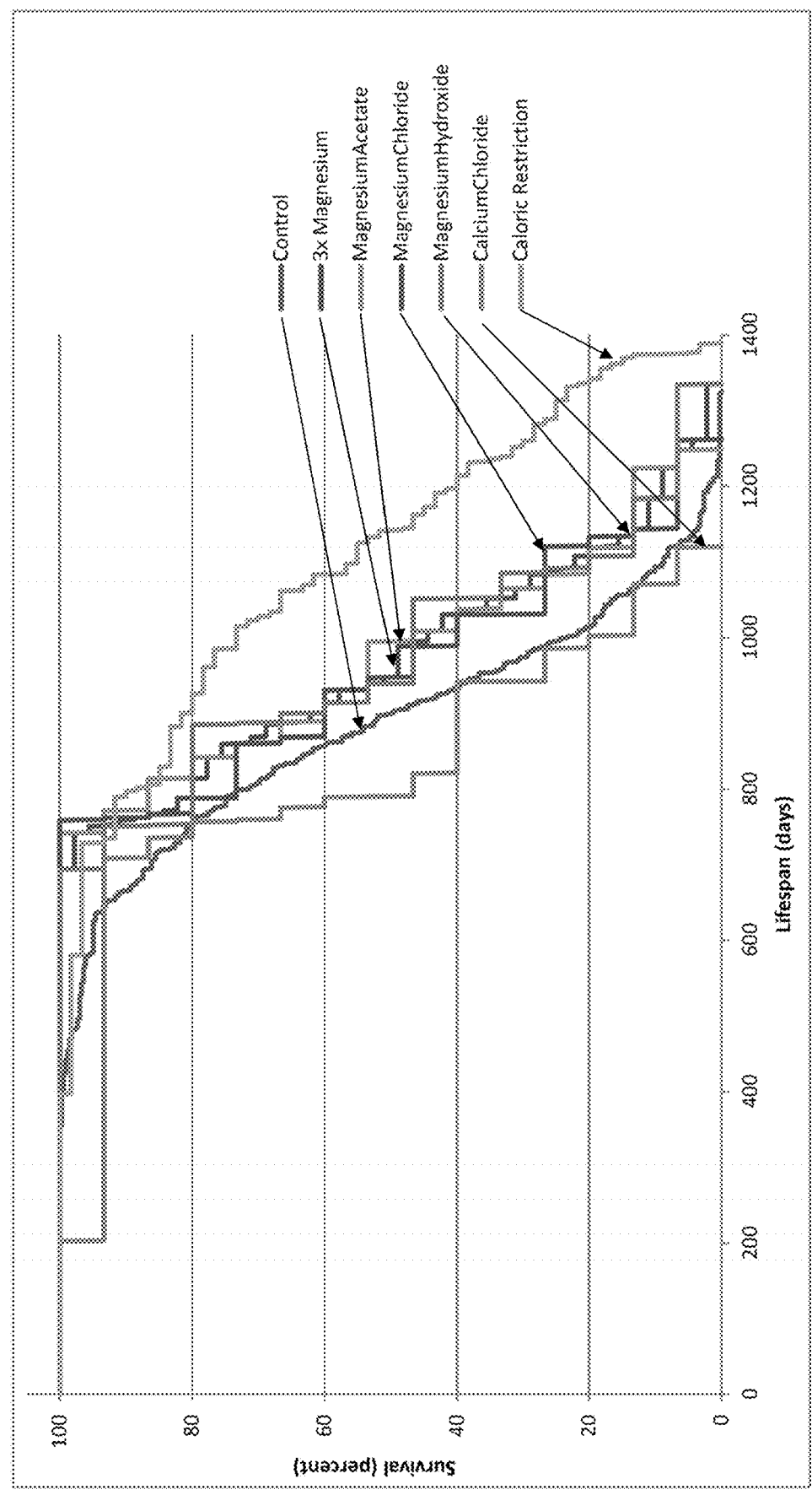
FIG. 7C depicts the effect of Magnesium ×3, Magnesium Hydroxide, Magnesium Acetate, Magnesium Chloride, Calcium Chloride on the lifespan of B6C3F1/J mice (also depicted is the effect of caloric restriction).

A third group of compounds that inventors have found exhibit significant lifespan extension are Magnesium compounds. Inventors performed the experiments as in Example 1 using Magnesium Acetate, Magnesium Chloride, Magnesium Hydroxide along with caloric restriction and Calcium Chloride. See FIGS. 7A, 7B and 7C. Inventors found that the Magnesium compounds significantly extended the life span of the mice. This class of compounds is thought to act on a different pathway from the pathways described in Example 1.

REFERENCES

Amador-Noguez et al., Alterations in xenobiotic metabolism in the long-lived Little mice. *Aging Cell* 6, 453 (2007).
Apostoli et al., "Elemental speciation in human health risk assessment" (United Nations Environment Programme, the International Labour Organization and the World Health Organization, www.who.int/ipcs/publications/ehc/ehc234.pdf, 2006).
Bartke et al., Somatotropic signaling: trade-offs between growth, reproductive development, and longevity. *Physiol Rev* 93, 571 (2013).
Benjamini et al., Controlling the false discovery rate: a practical and powerful approach to multiple testing. *Journal of the Royal Statistical Society. Series B (Methodological)* 57, 289 (1995).
Brandstadt et al., Lipid-lowering fibrates extend *C. elegans* lifespan in a NHR-49/PPARalpha-dependent manner. *Aging* 5, 270 (2013).
Buddington, et al., Non-digestible oligosaccharides and defense functions: lessons learned from animal models. *Br J Nutr* 87 Suppl 2, S231 (2002).
Gems et al., Broad spectrum detoxification: the major longevity assurance process regulated by insulin/IGF-1 signaling? *Mech Ageing Dev* 126, 381 (2005).
Gems et al., Genetics of longevity in model organisms: debates and paradigm shifts. *Annu Rev Physiol* 75, 621 (2013).
Gems et al., Stress-response hormesis and aging: "that which does not kill us makes us stronger". *Cell Metab* 7, 200 (2008).
Goldman et al., Substantial health and economic returns from delayed aging may warrant a new focus for medical research. *Health Aff (Millwood)* 32, 1698 (2013).
Guo et al., Induction of nuclear translocation of constitutive androstane receptor by peroxisome proliferator-activated receptor alpha synthetic ligands in mouse liver. *J Biol Chem* 282, 36766 (2007).
Hamelers et al., Steenbergh, Interactions between estrogen and insulin-like growth factor signaling pathways in human breast tumor cells. *Endocr Relat Cancer* 10, 331 (2003).
Harrison et al., Rapamycin fed late in life extends lifespan in genetically heterogeneous mice. *Nature* 460, 392 (Jul. 16, 2009).
Hewitt et al., Estrogen-mediated regulation of Igf1 transcription and uterine growth involves direct binding of estrogen receptor alpha to estrogen-responsive elements. *J Biol Chem* 285, 2676 (2010).
Kahlert et al., Estrogen receptor alpha rapidly activates the IGF-1 receptor pathway. *J Biol Chem* 275, 18447 (2000).
Kirkwood et al., Why do we age? *Nature* 408, 233 (2000).
Kirkwood, Evolution of ageing. *Nature* 270, 301 (1977).
Klang et al., Iron promotes protein insolubility and aging in *C. elegans*. *Aging* 6, 975 (2014).
Lipman et al., Lesion biomarkers of aging in B6C3F1 hybrid mice. *J Gerontol A Biol Sci Med Sci* 54, B466 (1999).
Macfarlane et al., Bacterial metabolism and health-related effects of galacto-oligosaccharides and other prebiotics. *J Appl Microbiol* 104, 305 (2008).
McElwee et al., Evolutionary conservation of regulated longevity assurance mechanisms. *Genome Biol* 8, R132 (2007).
McElwee et al., Shared transcriptional signature in Caenorhabditis elegans Dauer larvae and long-lived daf-2 mutants implicates detoxification system in longevity assurance. *J Biol Chem* 279, 44533 (2004).
Miller et al., Rapamycin, but not resveratrol or simvastatin, extends life span of genetically heterogeneous mice. *J Gerontol A Biol Sci Med Sci* 66, 191 (2011).
Nagai et al., Chelation: a fundamental mechanism of action of AGE inhibitors, AGE breakers, and other inhibitors of diabetes complications. *Diabetes* 61, 549 (2012).
Omiecinski et al., Xenobiotic metabolism, disposition, and regulation by receptors: from biochemical phenomenon to predictors of major toxicities. *Toxicol Sci* 120 Suppl 1, S49 (2011).
Price et al., Chelating activity of advanced glycation end-product inhibitors. *J Biol Chem* 276, 48967 (2001).

Reagan-Shaw et al., Dose translation from animal to human studies revisited. *FASEB J* 22, 659 (March, 2008).

Sauer et al., Products formed during fermentation of the prebiotic inulin with human gut flora enhance expression of biotransformation genes in human primary colon cells. *Br J Nutr* 97, 928 (May, 2007).

Sears, Chelation: harnessing and enhancing heavy metal detoxification—a review. *The Scientific World Journal* 2013, 219840 (2013).

Steinbaugh et al., Activation of genes involved in xenobiotic metabolism is a shared signature of mouse models with extended lifespan. *Am J Physiol Endocrinol Metab* 303, E488 (2012).

Tuohy, Inulin-type fructans in healthy aging. *J Nutr* 137, 2590S (2007).

Turturro et al., Growth curves and survival characteristics of the animals used in the Biomarkers of Aging Program. *J Gerontol A Biol Sci Med Sci* 54, B492 (1999).

Wen et al., Enhanced phase II detoxification contributes to beneficial effects of dietary restriction as revealed by multi-platform metabolomics studies. *Mol Cell Proteomics* 12, 575 (2013).

Yuan et al., Genetic regulation of life span, metabolism, and body weight in Pohn, a new wild-derived mouse strain. *J Gerontol A Biol Sci Med Sci* 68, 27 (2013).

Zhang et al., Structural modulation of gut microbiota in life-long calorie-restricted mice. *Nature communications* 4, 2163 (2013).

Zimniak et al., Detoxification reactions: relevance to aging. *Ageing Res Rev* 7, 281 (2008).

What is claimed is:

1. A method of prolonging the lifespan of a subject, the method comprising administering to the subject an effective amount of:
   (a) one or more compounds selected from: (i) clofibrate, and (ii) inulin; and
   (b) diethylenetriaminepentaacetic acid (DTPA)

wherein the lifespan to the subject is prolonged relative to the lifespan of the subject in the absence of the administration.

2. The method of claim 1 wherein (a) is inulin.

3. The method of claim 1, wherein (a) comprises clofibrate.

4. The method of claim 1 wherein the administration prolongs the lifespan of the subject more than the individual effect of the administration of either (a) or (b).

5. The method of claim 1 further comprising administering to the subject an effective amount of one or more compound selected from the group consisting of:
   (a) a COX inhibitor;
   (b) an antiparasitic agent;
   (c) an acetylcholinesterase inhibitor;
   (d) an adenosine receptor antagonist;
   (e) a selective estrogen receptor modulator.

6. The method of claim 1 further comprising administering to the subject an effective amount of:
   (i) a magnesium salt; and/or
   (ii) citric acid.

7. The method of claim 6 wherein the magnesium salt is Magnesium hydroxide, Magnesium acetate, or magnesium chloride.

8. The method of claim 1, wherein the subject is a human subject.

9. The method of claim 1, wherein (a) and (b) are administered over a period of at least 6 months.

10. The method of claim 1, wherein (a) and (b) are administered over a period of at least 12 months.

11. The method of claim 1, wherein (a) and (b) are administered over a period of at least 2 years.

* * * * *